US012564473B2

(12) United States Patent (10) Patent No.: US 12,564,473 B2
Randall et al. (45) Date of Patent: Mar. 3, 2026

(54) BIOPSY SITE MARKER HAVING MOVABLE PORTIONS

(71) Applicant: Devicor Medical Products, Inc., Cincinnati, OH (US)

(72) Inventors: Jack A. Randall, Cincinnati, OH (US); Garrett A. Householder, Cincinnati, OH (US); Xavier Robin, Karlsruhe (DE); Steffen Mueller, Gernsbach (DE); Bernd Vogel, Karlsruhe (DE)

(73) Assignee: Devicor Medical Products, Inc., Cincinnati, OH (US)

( * ) Notice: Subject to any disclaimer, the term of this patent is extended or adjusted under 35 U.S.C. 154(b) by 310 days.

(21) Appl. No.: 18/231,929

(22) Filed: Aug. 9, 2023

(65) Prior Publication Data

US 2024/0058093 A1     Feb. 22, 2024

Related U.S. Application Data

(60) Provisional application No. 63/398,338, filed on Aug. 16, 2022.

(51) Int. Cl.
    *A61B 90/00*          (2016.01)
(52) U.S. Cl.
    CPC ...... *A61B 90/39* (2016.02); *A61B 2090/3908* (2016.02); *A61B 2090/3987* (2016.02); *A61B 2090/3991* (2016.02)
(58) Field of Classification Search
    CPC .............. A61B 90/39; A61B 2090/3904–3995
    See application file for complete search history.

(56) References Cited

U.S. PATENT DOCUMENTS

| | | | |
|---|---|---|---|
| 6,056,700 | A | 5/2000 | Burney et al. |
| 6,083,524 | A | 7/2000 | Sawhney et al. |
| 6,162,241 | A | 12/2000 | Coury et al. |
| 6,270,464 | B1 | 8/2001 | Fulton, III et al. |
| 6,356,782 | B1 | 3/2002 | Sirimanne et al. |
| 6,605,294 | B2 | 8/2003 | Sawhney |
| 6,766,186 | B1 | 7/2004 | Hoyns et al. |
| 8,600,481 | B2 | 12/2013 | Sirimanne et al. |
| 8,939,910 | B2 | 1/2015 | Fisher |

(Continued)

FOREIGN PATENT DOCUMENTS

| | | | | |
|---|---|---|---|---|
| EP | 1948063 B1 * | 8/2010 | ............. | A61B 90/39 |
| EP | 3517068 B1 | 7/2021 | | |

OTHER PUBLICATIONS

International Search Report and Written Opinion dared Nov. 9, 2023 for Application No. PCT/US2023/029881, 11 pages.

(Continued)

*Primary Examiner* — Anh T Nguyen
*Assistant Examiner* — Younhee Choi
(74) *Attorney, Agent, or Firm* — FBT Gibbons LLP

(57) ABSTRACT

A biopsy site marker includes a marker element. The marker element includes a base portion and an anchor portion. The anchor portion extends from the base portion. The anchor portion includes a plurality of arms. One or more arms of the plurality of arms is configured to be responsive to heat to transition from a pre-deployment configuration to a post-deployment configuration. Each transitioned arm of the plurality of arms extending outwardly from a longitudinal axis defined by the marker element when in the post-deployment configuration.

17 Claims, 14 Drawing Sheets

(56)  References Cited

U.S. PATENT DOCUMENTS

| 11,219,612 | B2 | | 1/2022 | Liu |
| 2006/0235295 | A1 | | 10/2006 | Boese et al. |
| 2009/0216263 | A1 | * | 8/2009 | Tekulve ........... A61B 17/12022 |
| | | | | 606/200 |
| 2019/0076212 | A1 | * | 3/2019 | Liu ........................ A61B 90/39 |
| 2019/0223975 | A1 | * | 7/2019 | Agostinelli ............ A61B 5/062 |
| 2020/0054413 | A1 | * | 2/2020 | Vogel ..................... A61B 90/39 |
| 2023/0000585 | A1 | * | 1/2023 | Hornscheidt .......... A61B 90/39 |

OTHER PUBLICATIONS

International Search Report and Written Opinion dared Nov. 9, 2023 for Application No. PCT/US2023/029882, 13 pages.

\* cited by examiner

BIOPSY SITE MARKER HAVING MOVABLE PORTIONS

PRIORITY

This application claims priority to U.S. Provisional Application Ser. No. 63/398,338, entitled "Biopsy Site Marker Having Movable Portions," filed on Aug. 16, 2022, the disclosure of which is incorporated by reference herein.

BACKGROUND

Breast biopsies may be performed because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MM) or x-ray may be used to locate the biopsy site. In order to assist the relocation of the biopsy site, a marker may be placed at the time of the biopsy.

The use of markers used after breast biopsies to mark the location where the biopsied tissue was removed is described in the following US Patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

Once a marker is placed at a biopsy site, the marker can later be relocated to identify the biopsy site in subsequent follow-up procedures. In some contexts, a placed marker may not completely correspond to the biopsy site when the marker is relocated. For instance, the marker may migrate to another nearby location during the intervening time between the biopsy procedure and subsequent follow up procedures. Migration of the biopsy site marker may cause difficulties when identifying the biopsy site during subsequent follow-up procedures. Accordingly, it may be desirable to incorporate features into a marker to maintain the marker in a fixed position over time.

While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
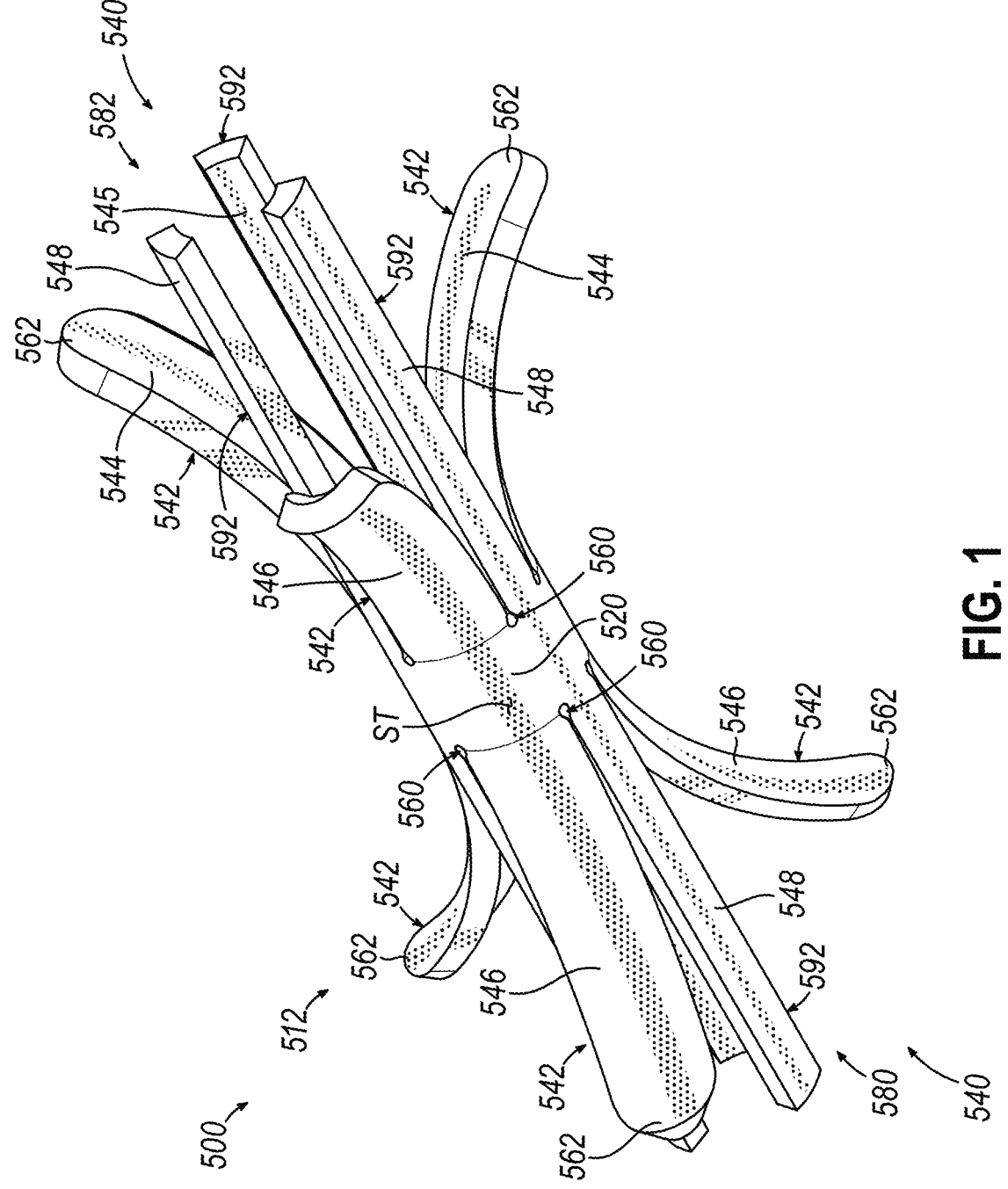
FIG. 1 depicts a perspective view of an example of a biopsy site marker.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

III. EXAMPLES OF BIOPSY SITE MARKERS FOR LIMITED MIGRATION

In some versions of a biopsy site marker it may be desirable to include certain features within the marker to reduce the propensity of the marker to migrate when placed within tissue. For instance, some markers may be prone to migration after placement at a biopsy site due to movement of tissue in the intervening time between marker placement and subsequent follow-up procedures. As a result, such markers may introduce challenges with accurately identifying the biopsy site during subsequent follow-up procedures. Accordingly, it may be desirable to incorporate features into a marker to assist in maintaining the marker in a fixed position within tissue over time. Although several versions are described herein that incorporate the features described above, it should be understood that various alternative combinations can be used without departing from the basic principles described herein.

A. Example of Biopsy Site Marker with Central Base Portion

FIG. 1 shows an exemplary marker (500) that is generally configured to expand from a pre-deployment configuration to a post-deployment configuration to thereby anchor marker (500) within tissue. Marker (500) of the present version includes a marker element (512). In some versions, marker element (512) can be substantially similar to marker element (12) described in greater detail below. Thus, marker element (512) can be generally configured as non-bioabsorbable and radiopaque and/or echogenic to enhance visualization over time. Additionally, although not shown, it should be understood that in some versions, marker (500) may include structures similar to carrier (120) described in greater detail below. In versions including structures similar to carrier (120), such structures may be shaped as described below or alternatively configured as a coating. In other versions, marker (500) may only include marker element (512), omitting structures similar to carrier (120) described below. In other words, in some versions, marker (500) may be configured as a "bare" marker.

Marker (500) of the present version is configured to transition from a pre-deployment configuration to a post-deployment configuration after being deployed at a biopsy site. Marker (500) includes a base portion (520) and an anchor portion (540), with both base portion (520) and anchor portion (540) being defined by marker element (512). Base portion (520) defines a generally cylindrical shape. In the present version, base portion (520) is hollow and defines an open proximal end (522) (see FIG. 4) on each proximal and distal side of base portion (520). In other versions, base portion (520) may be partially or substantially solid.

Anchor portion (540) includes a distal anchor portion (580) and a proximal anchor portion (582) extending distally and proximally from base portion (520), respectively. In other words, base portion (520) is disposed between distal anchor portion (580) and proximal anchor portion (582). Additionally, the hollow interior of base portion (520) may be open to the interior of distal anchor portion (580) and proximal anchor portion (582). As will be described in greater detail below, anchor portion (540) is generally configured to transition from a pre-deployment configuration to a post-deployment configuration in response to one or more environmental stimuli.

Although reference to "anchor" in anchor portion (540) herein may suggest that only anchor portion (540) may serve to anchor marker (500) within tissue, it should be understood that other features of marker (500) may also be used to facilitate anchoring in tissue. Such anchoring functionality may be present even if a feature is not referred to herein directly using the term "anchor" or similar terms. For instance, under some circumstances, one or more portions of base portion (520) may also have an anchoring function by facilitating the growth of tissue into marker (500). In addition, or in the alternative, some versions of marker (500) may include structures similar to carrier (120), which may expand within tissue and serve to further facilitate anchoring of marker (500) within tissue.

Each of distal anchor portion (580) and proximal anchor portion (582) of the present version include a plurality of active arms (542) (also referred to as movable arms, engagement arms, or anchor arms) and a plurality inactive arms (592) (also referred to as passive arms, stationary arms, or straight arms) extending outwardly away from base portion (520) along a longitudinal axis defined by marker element (512). Arms (542, 592) are together oriented in a circular pattern corresponding to the cylindrical shape of base portion (520). Around the circular pattern, arms (542, 592) are arranged in an alternating configuration—alternating between active arm (542) and inactive arm (592). In other words, arms (542, 592) are arranged such that there is an inactive arm (592) positioned between each active arm (542).

Although the present version includes three active arms (542) and three inactive arms (592), it should be understood that in other versions other suitable numbers of arms (542, 592) may be used such as two, four, five, etc. In addition, or in the alternative, in other versions, any suitable number of combinations of arms (542, 592) may be used rather than three of active arms (542) and three of inactive arms (592). In still other versions, distal anchor portion (580) may have any one of the above-described configurations of arms (542, 592), while proximal anchor portion (582) may have another one of the above described configurations of arms (542, 592). Each arm (542, 592) is defined by a plurality of slots extending from the distal end of marker element (512) to base portion (520). As will be described in greater detail below, one or more of arms (542, 592) are generally configured to move from a pre-deployment position to a post-deployment position. For reference, the post-deployment position is shown in FIG. 1.

Each arm (542, 592) defines a generally semi-cylindrical cross-sectional shape such that each arm (542, 592) may be abutted with each adjacent arm (542, 592) to form a cylindrical shape corresponding to the shape of base portion (520). In particular, each arm (542, 592) includes a curved inner surface (544, 545) and a curved outer surface (546, 548), respectively. Thus, when each arm (542, 592) is positioned to abut each adjacent arm (542, 592), curved surfaces (544, 545, 546, 548) together form a cylindrical inner and outer surface.

The inner end of each arm (542, 592) is secured to a respective outer end of base portion (520) such that each arm (542, 592) extends outwardly from base portion (520). In the present version, each arm (542, 592) is integral with base portion (520), although in other versions, each arm (542, 592) may be fixedly secured to base portion (520).

Figure 2:
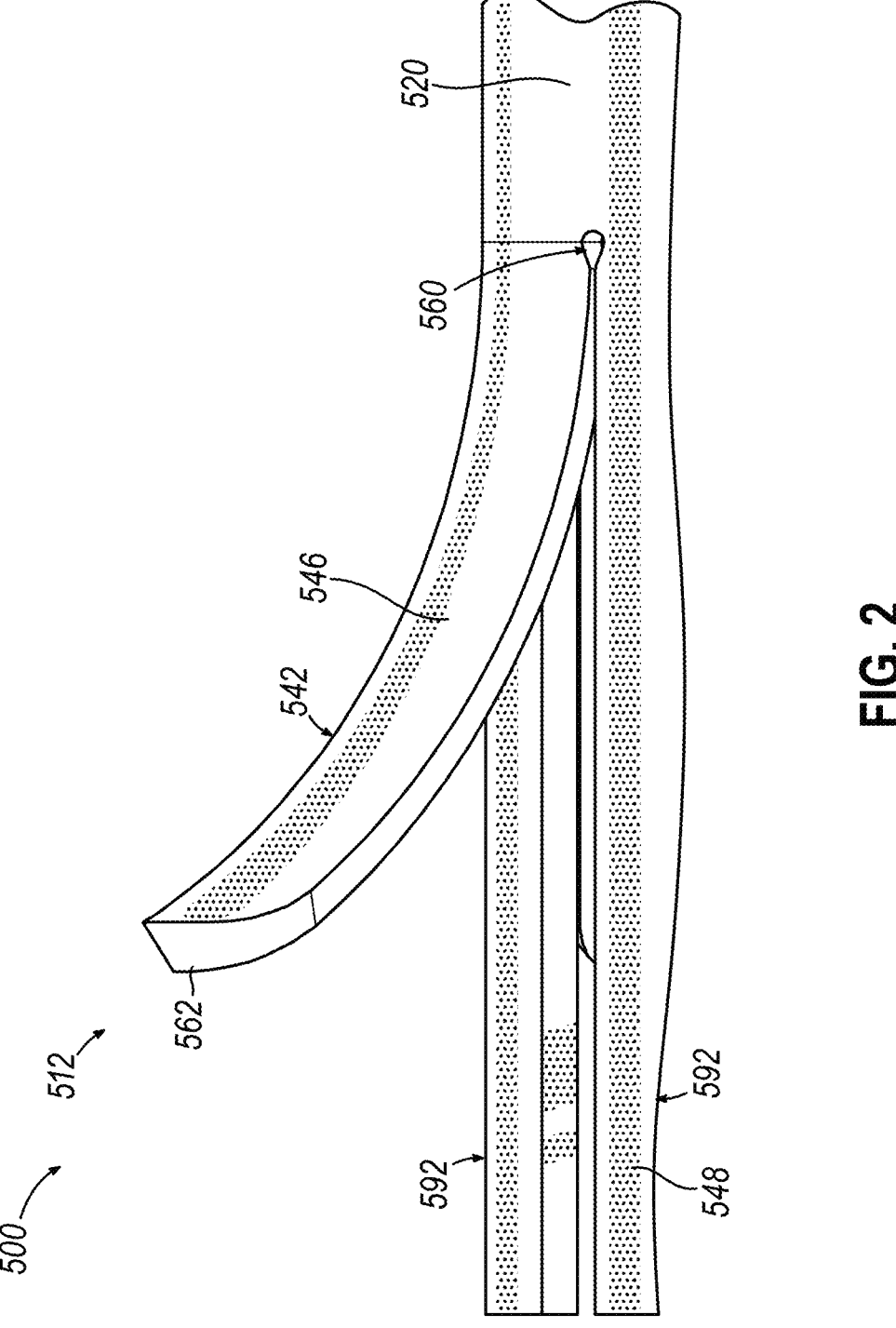
FIG. 2 depicts a detailed side elevational view of the marker of FIG. 1.

Base portion (520) and/or a portion of each arm (542, 592) defines a plurality of relief openings (560). As best seen in FIG. 2, each relief opening (560) defines a generally tear-dropped or round-shaped configuration. Each relief opening (560) further extends entirely through the surface of base portion (520) and/or a portion of each arm (542, 592) into a hollow interior of marker element (512). As will be described in greater detail below, each relief opening (560) is configured to promote flexion of each active arm (542) relative to base portion (520) and each adjacent arm (542, 592).

The outer end of each active arm (542) includes a tip (562) having a blunt configuration. In particular, all edges of each active arm (542) intersecting at tip (562) are generally rounded or otherwise blended together such that tip (562) of each active arm (542) is generally atraumatic in configuration. Such a configuration may be desirable in some versions to promote movement of active arms (542) through tissue either during deployment or after deployment. For instance, during deployment, the blunt configuration of each tip (562) may be desirable to promote ease of movement through various instruments, devices, and/or tissue. Similarly, after deployment, the blunt configuration of each tip (562) may promote movement arms (542) through tissue so that movement is not impeded and surrounding tissue is not damaged unnecessarily. Although each inactive arm (592) includes a cutoff or flat distal end in the present version, it should be understood that in other versions, each inactive arm (592) may include an end having a blunt configuration similar to tip (562) described above with respect to active arms (542).

In the present version, active arms (542) define a shorter length of extension from base portion (520) than inactive arms (592). In other words, active arms (542) are generally shorter than inactive arms (592). As will be described in greater detail below, this feature may be desirable to promote the transition of active arms (542) from a pre-deployment configuration to a post-deployment configuration. In other versions, the length of active arms (542) may be substantially identical to the length of inactive arms (592). Moreover, although each active arm (542) has a substantially identical length relative to each other active arm (542), and each inactive arm (592) has a substantially identical length relative to each other inactive arm (592), it should be understood that in some versions, the individual length of each active arm (542) and/or inactive arm (592) may be varied. For instance, in some versions, one or more active arms (542) may be longer than other active arms (542). Similarly, one or more inactive arms (592) may be longer than other inactive arms (592). Still other variations of the configuration of each arm (542, 592) relative to other arms (542, 592) will be apparent to those of ordinary skill in the art in view of the teachings herein.

Marker element (512) of the present version generally has a mirrored configuration with arms (542, 592) projecting from each side of base portion (520) in a substantially similar configuration. In other words, arms (542, 592) on a proximal side of marker element (512) form a mirror image of arms (542, 592) on a distal side of marker element (512) with base portion (520) being positioned at the center of marker element (512). However, it should be understood that in other versions, various non-symmetrical or non-mirrored configurations may be used. For instance, in some versions, arms (542, 592) may only extend from a single side of base portion (520). In other versions, arms (542, 592) on one side of marker element (512) may be longer relative to arms (542, 592) on another side of marker element (512). Thus, in some versions, base portion (520) may be positioned off-center relative to arms (542, 592).

As noted above, active arms (542) may move between a pre-deployment configuration and a post-deployment configuration. Meanwhile, inactive arms (592) may remain generally stationary during the transition of active arms (542) from the pre-deployment configuration to the posit deployment configuration. FIGS. 1 and 2 show active arms (542) in the post-deployment state. In this state, each active arm (542) curves outwardly from a longitudinal axis defined by marker element (512). In other words, active arms (542) may be splayed outwardly relative to each other. Also in this state, inactive arms (592) remain in a generally straight configuration, extending along the longitudinal axis defined by marker element (512). In some versions, the outward extension, curvature, and/or splaying of active arms (542) may approximately double the diameter of marker (500) relative to the diameter when in the pre-deployment configuration. In other versions, this outward extension, curvature, and/or splaying of active arms (542) may approximately triple the diameter of marker (500) relative to the diameter when in the pre-deployment configuration.

As best seen in FIG. 2, the particular outward curvature of each active arm (542) may be non-linear with the curvature having a relatively low slope initially, followed by a relatively high slope. In other words, the curvature of each active arm (542) may be approximately exponential. In other versions, each active arm (542) may be configured with a curvature having one or more inflection points such that active arms (542) may have a more irregular shape relative to the continuously increasing slope shown. In addition, or in the alternative, in some versions, the particular curvature used may be varied among active arms (542), with one or more active arms (542) having an irregular curvature and one or more other active arms (542) having a relatively continuous curvature similar to the one shown in FIG. 2.

As described above, arms (542, 592) of the present version are integral with base portion (520). Marker element (512) is thus a single monolithic, homogeneous continuum of material. The particular material used in the present version is a shape-memory alloy. As will be described in greater detail below, the shape-memory characteristic of the material used in marker element (512) may be used to permit transitioning of active arms (542) from the pre-deployment configuration to the post-deployment configuration using patient heat from tissue surrounding the biopsy site to initiate the transition.

It should be understood that a variety of suitable shape-memory alloys may be used for marker element (512). In addition, the constituents of any one shape-memory alloy may be varied to produce desired properties (e.g., transformation temperature). One suitable shape-memory alloy may include Nitinol (nickel-titanium). Any suitable grade of Nitinol may be used. By way of example only, one suitable grade of Nitinol may include Nitinol S (ASTM 2063). Alternatively, other shape-memory alloys may include copper-based alloys, gold-cadmium, silver-cadmium, and/or nickel-aluminum.

Returning to FIG. 1, the entire outer surface of marker element (512) may include a surface treatment (ST). Surface treatment (ST) is generally configured to enhance the echogenicity of marker element (512). In the present version, surface treatment (ST) includes a roughened surface texture caused by sandblasting. However, it should be understood that in other versions, various alternative surface treatments (ST) may be used. For instance, in some versions, surface treatment (ST) may include an echogenic coating having a plurality of microspheres and a polymer binder. Such a coating may be in addition to, or in lieu of, sandblasting. In addition, or in the alternative, other versions may include a roughened surface by various processing mechanisms such as peening, griding, knurling, and/or etc. Of course, various alternative configurations of surface treatment (ST) may be used as will be apparent to those of ordinary skill in the art in view of the teachings herein.

Figure 3B:
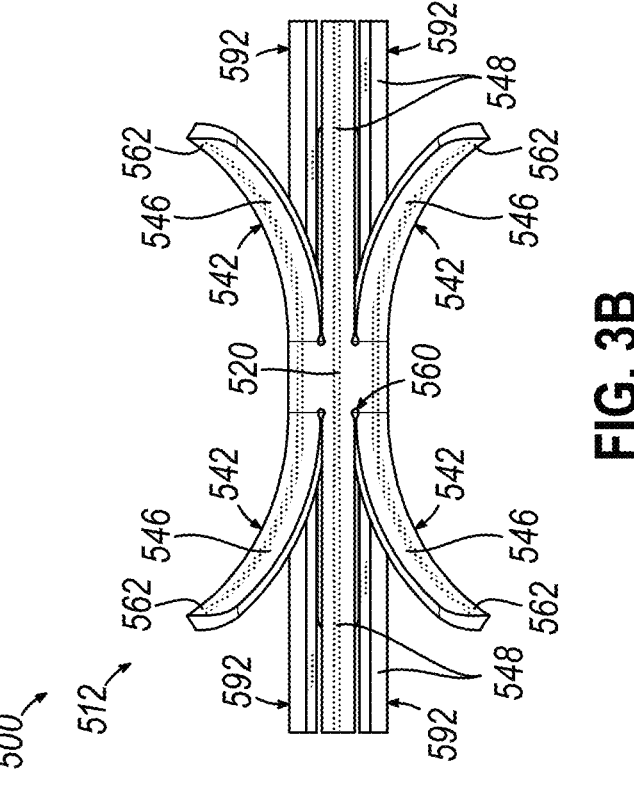
FIG. 3B depicts another side elevational view of the marker of FIG. 1, the marker being in a post-deployment configuration.
Figure 3A:
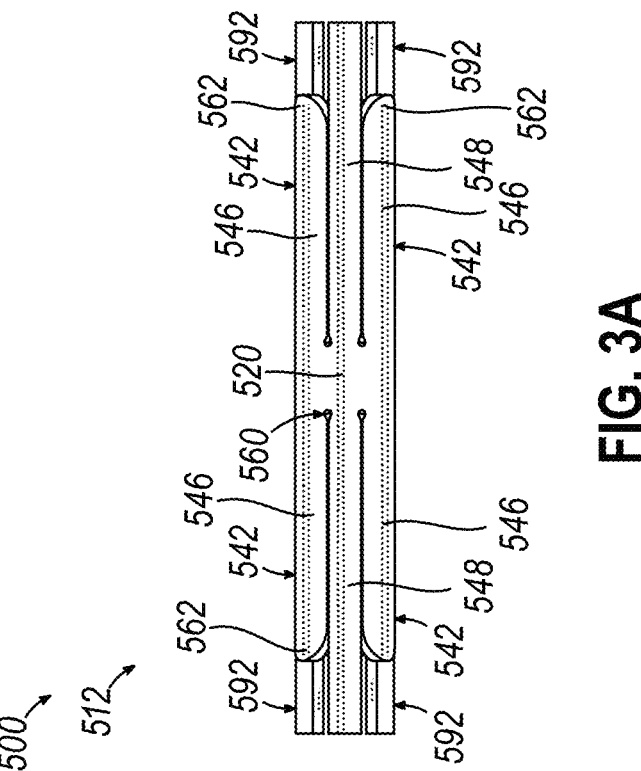
FIG. 3A depicts a side elevational view of the marker of FIG. 1, the marker being in a pre-deployment configuration.
Figure 4:
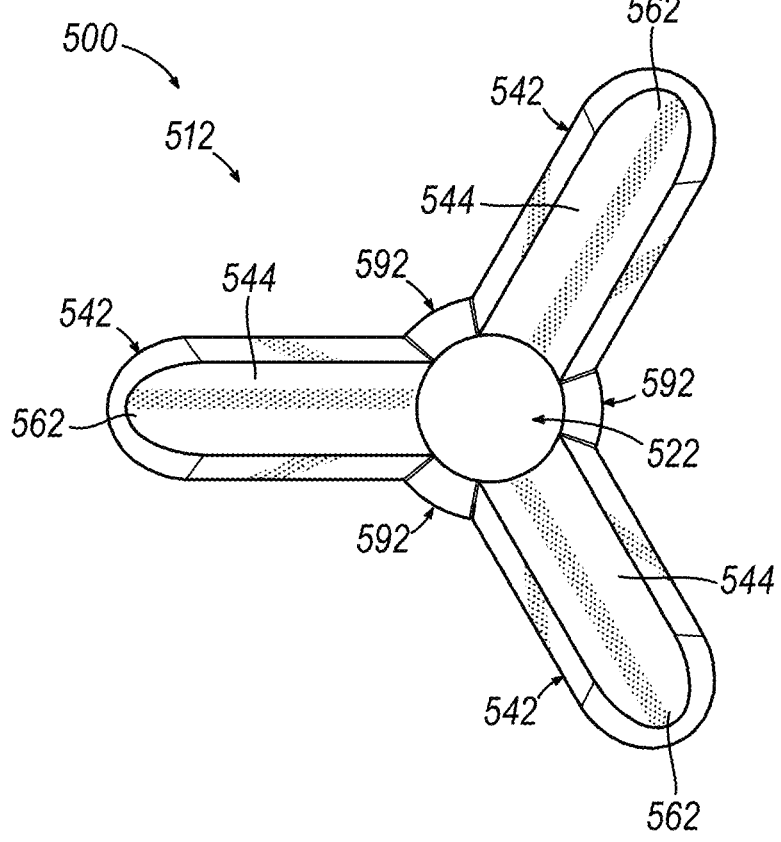
FIG. 4 depicts a front elevational view of the marker of FIG. 1, the marker being in the post-deployment configuration of FIG. 3B.

FIGS. 3A through 4 show aspects of a use of marker element (512) for marking tissue. As can be seen in FIG. 3A, marker element (512) may initially begin with active arms (542) in the pre-deployment configuration. In the pre-deployment configuration, active arms (542) may be compressed inwardly towards the longitudinal axis defined by marker element (512) so that each active arm (542) abuts each adjacent inactive arm (592). When active arms (542) are compressed as shown, arms (542, 592) together form a generally hollow cylindrical shape corresponding to the shape of base portion (520). Thus, marker element (512) may define a generally cylindrical shape when active arms (542) are in the pre-deployment configuration.

In some versions, the post-deployment configuration described above may correspond to a "natural," "original," "shape set," or "undeformed" shape. In other words, the post-deployment configuration may be the natural or as-manufactured shape of active arms (542) imparted into the shape-memory alloy. Active arms (542) may then be compressed into the pre-deployment shape shown in FIG. 3A subsequently during manufacturing to prepare marker element (512) for use in deployment at a biopsy site.

Regardless of how the transformation of active arms (542) to the pre-deployment configuration is performed, marker element (512) may be introduced into a patient at a biopsy site while in the pre-deployment configuration. In some uses, introduction of marker element (512) may be performed using marker delivery device (150) described in greater detail below. The pre-deployment configuration may be desirable for introduction at the biopsy site because the compact and uniform shape may promote use with instruments similar to marker delivery device (150) described below. The compact and uniform shape may also promote movement of marker element (512) through tissue for placement at the biopsy site.

Once marker element (512) is positioned as desired, marker element (512) may absorb heat from the tissue adjacent to the biopsy site and increase in temperature. The temperature of marker element (512) may increase until reaching a transformation temperature of the shape-memory alloy of marker element (512). Once the transformation temperature is reached, the alloy may return to its natural, original, or undeformed shape. In the present version, this shape corresponds to the post-deployment configuration of active arms (542). Thus, heat from the patient may initiate a transition of active arms (542) from the pre-deployment configuration to the post-deployment configuration.

As best seen in FIGS. 3B and 4, the transition to the post-deployment configuration includes active arms (542) moving away from the longitudinal axis defined by marker element (512). In other words, active arms (542) may spread or splay outwardly relative to each other. During this transition, active arms (542) may engage the tissue surrounding the biopsy site to anchor marker element (512) in the tissue, thereby holding marker element (512) in position at the biopsy site.

Throughout the transition of active arms (542) from the pre-deployment configuration to the post-deployment configuration, inactive arms (592) remain generally stationary. In particular, as best seen in FIGS. 3A and 3B, inactive arms (592) generally remain in a straight configuration throughout the transition of active arms (542) from the pre-deployment configuration to the post-deployment configuration. In this straight configuration of inactive arms (592), inactive arms (592) remain in a position extending along a longitudinal axis defined by marker element (512). In some versions, the configuration of inactive arms (592) in the straight and static configuration shown may be desirable to promote anchoring of marker (500). For instance, inactive arms (592) may set and hold an initial position of maker (500) by engaging tissue adjacent to the proximal and distal ends of marker. This initial position of marker (500) may then be held by inactive arms (592) until active arms (542) fully engage adjacent tissue via the transition from the pre-deployment configuration to the post-deployment configuration.

Figure 5:
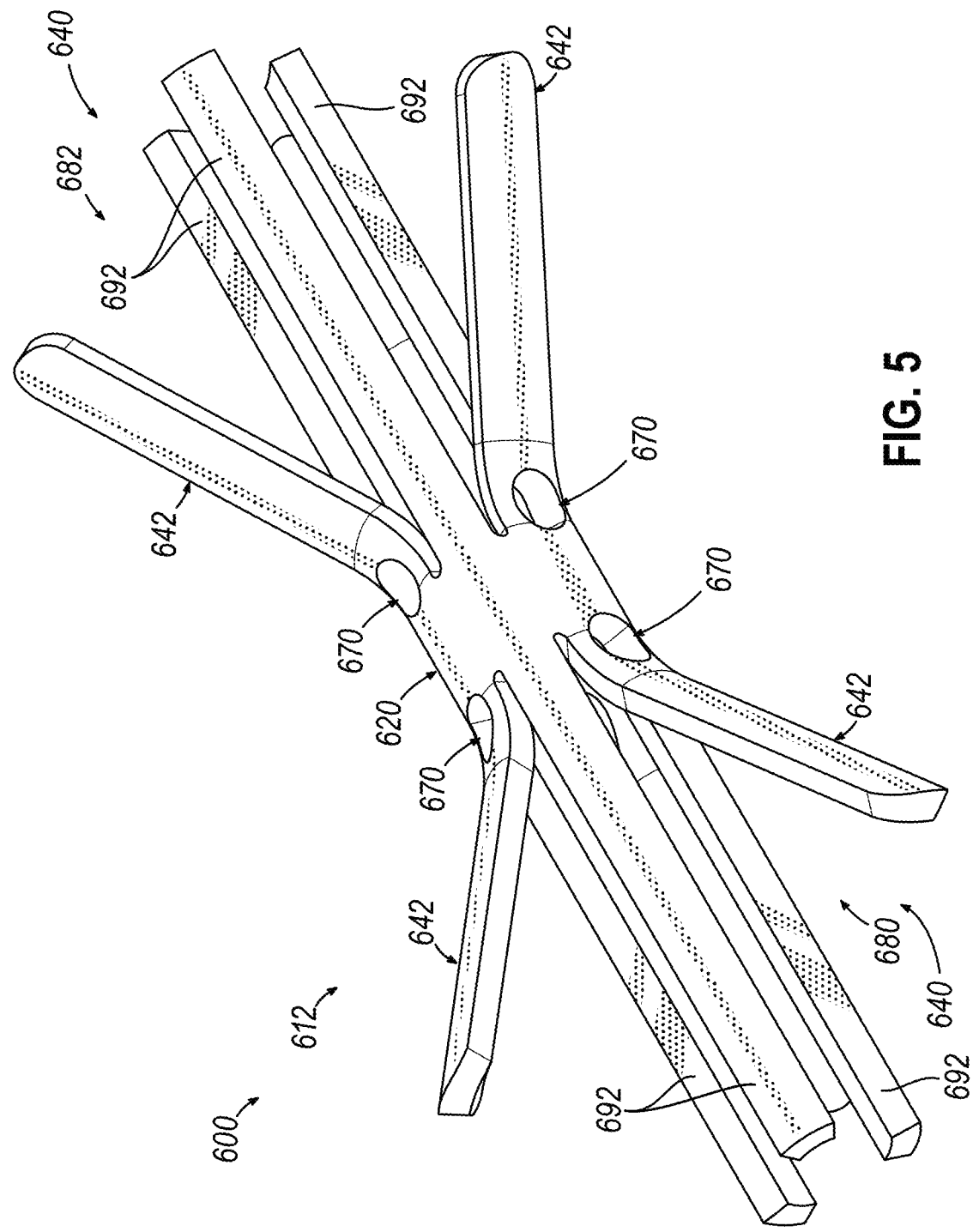
FIG. 5 depicts a perspective view of another example of a biopsy site marker.

FIG. 5 shows another version of a biopsy site marker (600) that is substantially similar to marker (500) described above. For instance, like marker (500) described above, marker (600) of the present version includes a marker element (612) that may be used as a "bare" marker or in connection with structures similar to carrier (120) described below. As with marker element (512) described above, marker element (612) of the present version includes a base portion (620) with an anchor portion (640) extending outwardly from base portion (620) along a longitudinal axis defined by marker element (612). As similarly described above with respect to anchor portion (540), anchor portion (640) of the present version includes both a distal anchor portion (680) and a proximal anchor portion (682).

Both distal anchor portion (680) and proximal anchor portion (682) include a set of active arms (642) and a set of inactive arms (692) extending outwardly from base portion (620). Except as otherwise described below, arms (642, 692) are configured and function as similarly described above with respect to arms (542, 592). For instance, as with arms (542, 592) described above, arms (642, 692) of the present version may be configured such that active arms (642) may transition from a pre-deployment configuration to a post-deployment configuration, while inactive arms (692) remain in a generally stationary or static configuration.

Unlike active arms (542) described above, each active arm (642) of the present example includes a one or more openings (670) extending through the surface of each active arm (642) and in communication with a hollow interior of marker element (612). In the present version, each active arm (642) includes one opening (670), although multiple openings (670) may be used in other versions. Opening (670) in each active arm (642) is positioned proximate base portion (620) and in some versions may overlap with at least a portion of base portion (620). In some versions, openings (670) may be configured to promote the growth of tissue into marker element (612). In addition, or in the alternative, in some versions, openings (670) may be configured to provide enhanced visualization by providing enhanced echogenicity under for visualization under ultrasound or a more visible shape under x-ray.

Unlike active arms (542) described above, active arms (642) of the present example define a different shape in the post-deployment configuration. Specifically, FIG. 5 shows the post-deployment configuration of active arms (642). As can be seen, active arms (642) define a generally straight but angled configuration when in the post-deployment configuration. In other words, rather than being curved, active arms (642) may form a linear shape having a constant slope away from the longitudinal axis defined by marker element (612). Although a generally linear shape having only one slope is shown in the present version, it should be understood that in other versions, a plurality of single slopes may be used with one section of each active arm (642) extending at a first angle and one or more other sections of each active arm (642) extending at a second angle different from the first angle.

B. Example of Biopsy Site Marker with Central Anchor Portion

Figure 6:
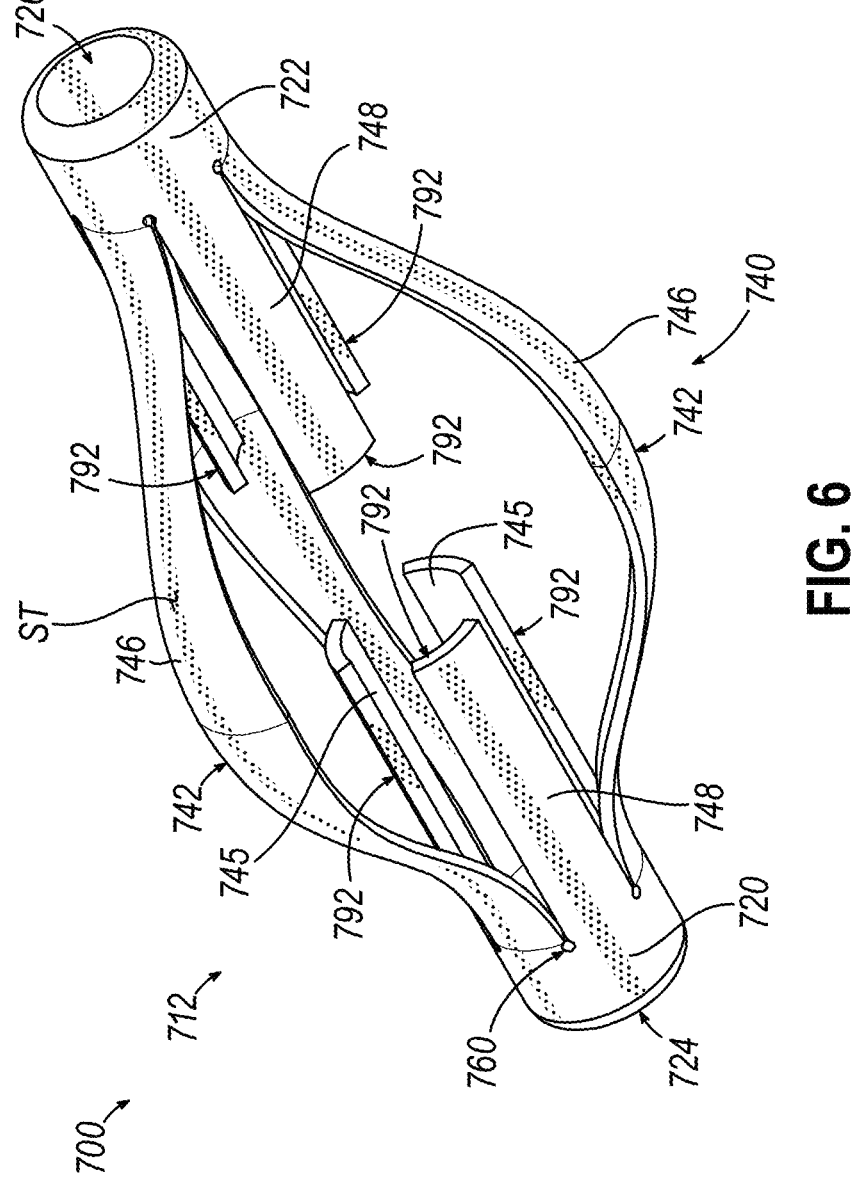
FIG. 6 depicts a perspective view of yet another example of a biopsy site marker.

FIG. 6 shows another exemplary biopsy site marker (700) that is generally configured to expand from a pre-deployment configuration to a post-deployment configuration to thereby anchor marker (700) within tissue. In some versions, marker (700) is similar to markers (500, 600) described above or marker (100) described below. For instance, like with markers (500, 600), marker (700) of the present version includes a marker element (712). In some versions, marker element (712) can be generally configured as non-bioabsorbable and radiopaque and/or echogenic to enhance visualization over time. Additionally, although not shown, it should be understood that in some versions, marker (700) may include structures similar to carrier (120) described below. In versions including structures similar to carrier (120), such structures may be shaped as described above or alternatively configured as a coating. In other versions, marker (700) may only include marker element (712), omitting structures similar to carrier (120) described below. In other words, in some versions, marker (700) may be configured as a "bare" marker.

Marker (700) of the present version is configured to transition from a pre-deployment configuration to a post-deployment configuration after being deployed at a biopsy site. Marker (700) includes a distal base portion (720), a proximal base portion (722), and an anchor portion (740) extending between base portions (720). Both base portions (720, 722) and anchor portion (740) are defined by marker element (712) in the present example. Each base portion (720, 722) defines a generally cylindrical shape. In the present version, each base portion (720, 722) is hollow and defines a respective open end (724, 726) on the outer side of each base portion (720, 722). In other versions, each base portion (720, 722) may be partially or substantially solid.

Anchor portion (740) extends between each base portion (720, 722) from a distal portion of marker element (712) to a proximal portion of marker element (712). In other words, each base portion (720, 722) is disposed on a respective end of anchor portion (740). Additionally, the hollow interior of each base portion (720, 722) may be open to the interior of anchor portion (740). As will be described in greater detail below, anchor portion (740) is generally configured to transition from a pre-deployment configuration to a post-deployment configuration in response to one or more environmental stimuli.

Anchor portion (740) present version include a plurality of active arms (742) (also referred to as movable arms, engagement arms, or anchor arms) and a plurality inactive arms (792) (also referred to as passive arms, stationary arms, static arms, or straight arms) extending inwardly from each base portion (720, 722) along a longitudinal axis defined by marker element (712). Arms (742, 792) are together oriented in a circular pattern corresponding to the cylindrical shape of each base portion (720, 722). Around the circular pattern, arms (742, 792) are arranged in an alternating configuration—alternating between active arm (742) and inactive arm (792). In other words, arms (742, 792) are arranged such that there is an inactive arm (792) positioned between each active arm (742).

The present version includes three active arms (742) and six inactive arms (782). In particular, each active arm (742) extends entirely from distal base portion (720) to proximal base portion (722), thereby defining a continuous section of material connecting distal base portion (720) to proximal base portion (722). Meanwhile, each inactive arm (782) extends inwardly from only either distal base portion (720) or proximal base portion (722). In other words, each inactive arm (782) includes a broken section of material between distal base portion (720) and proximal base portion (722). In some versions, this broken configuration of inactive arms (782) may be desirable to provide at least some freedom of movement with respect to active arms (742), as will be described in greater detail below.

Although the present version includes three active arms (742) and six inactive arms (792), it should be understood that in other versions other suitable numbers of arms (742, 792) may be used such as two, four, five, etc. In addition, or in the alternative, in other versions, any suitable number of combinations of arms (742, 792) may be used rather than three of active arms (742) and three of inactive arms (792).

Each arm (742, 792) is defined by a plurality of slots extending from distal base portion (720) to proximal base portion (722). As will be described in greater detail below, one or more of arms (742, 792) are generally configured to move from a pre-deployment position to a post-deployment position. For reference, the post-deployment position is shown in FIG. 6.

Each arm (742, 792) defines a generally semi-cylindrical cross-sectional shape such that each arm (742, 792) may be abutted with each adjacent arm (742, 792) to form a cylindrical shape corresponding to the shape of base portions (720, 722). In particular, each arm (742, 792) includes a curved inner surface (744, 745) and a curved outer surface (746, 748), respectively. Thus, when each arm (742, 792) is positioned to abut each adjacent arm (742, 792), curved surfaces (744, 745, 746, 748) together form a cylindrical inner and outer surface.

Figure 7:
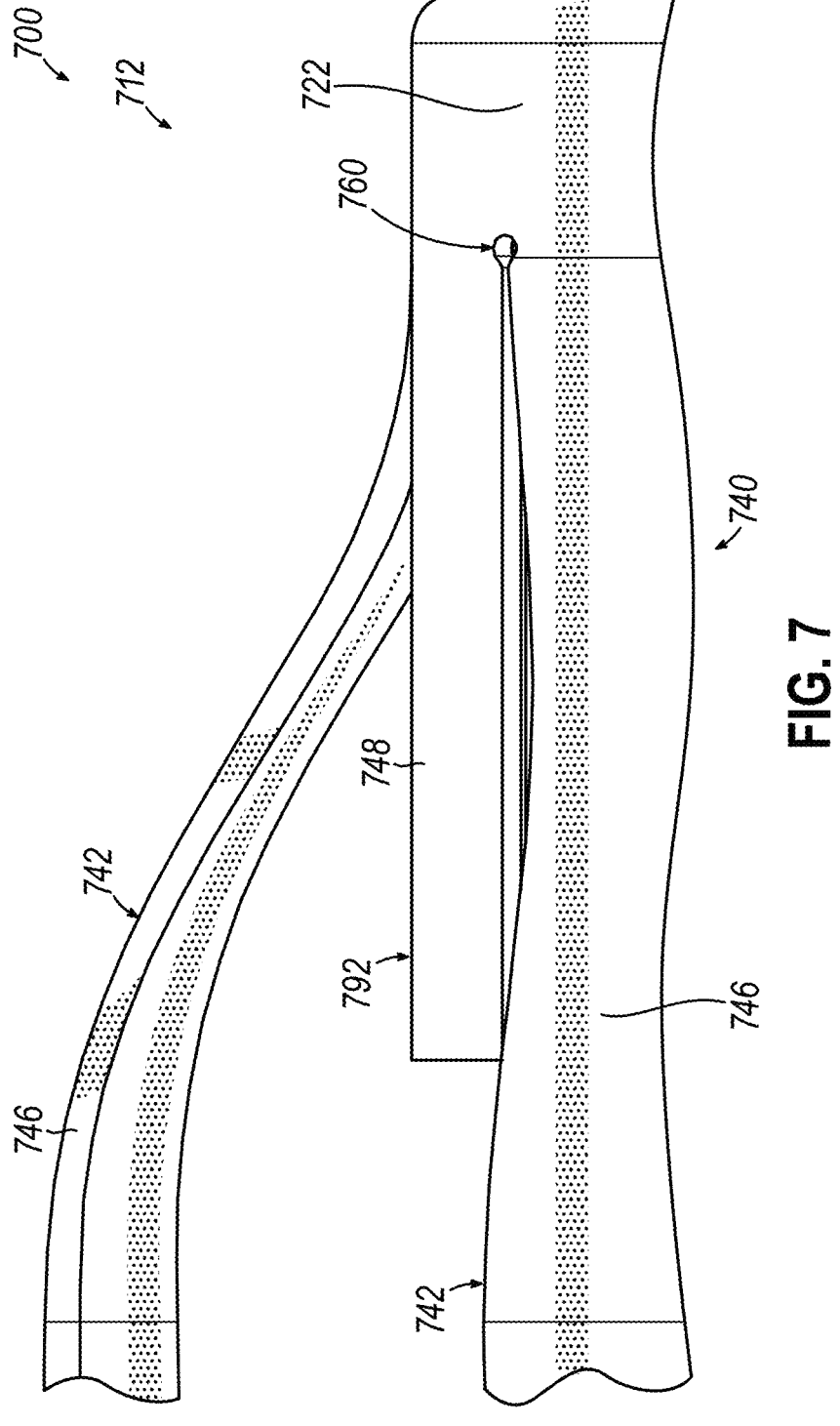
FIG. 7 depicts a detailed side elevational view of the marker of FIG. 6.

Base portions (720, 722) and/or a portion of each arm (742, 792) define a plurality of relief openings (760). As best seen in FIG. 7, each relief opening (760) defines a generally tear-dropped or round-shaped configuration. Each relief opening (760) further extends entirely through the surface of base portions (720, 722) and/or a portion of each arm (742, 792) into a hollow interior of marker element (712). As will be described in greater detail below, each relief opening (760) is configured to promote flexion of each active arm (742) relative to base portions (720) and each adjacent arm (742, 792).

In the present version, active arms (742) define a longer length of extension between each base portion (720, 722) relative to each inactive arm (792). In other words, inactive arms (792) are generally shorter than active arms (742). As will be described in greater detail below, this feature may be desirable to promote the transition of active arms (742) from a pre-deployment configuration to a post-deployment configuration. In other versions, the length of active arms (742) may be substantially identical to the length of inactive arms (792). Moreover, although each active arm (742) has a substantially identical length relative to each other active arm (742), and each inactive arm (792) has a substantially identical length relative to each other inactive arm (792), it should be understood that in some versions, the individual length of each active arm (742) and/or inactive arm (792) may be varied. For instance, in some versions, one or more active arms (742) may be longer than other active arms (742). Similarly, one or more inactive arms (792) may be longer than other inactive arms (792). Still other variations of the configuration of each arm (742, 792) relative to other arms (742, 792) will be apparent to those of ordinary skill in the art in view of the teachings herein.

Marker element (712) of the present version generally has a mirrored configuration with arms (742, 792) projecting inwardly from each base portion (720, 722) in a substantially similar configuration. In other words, each active arm (742) extends from one side of marker element (712) to another, while inactive arms (792) extend from each base portion (720, 722) in an identical, but mirror image configuration. However, it should be understood that in other versions, various non-symmetrical or non-mirrored configurations may be used. For instance, in some versions, arms (742, 792) may only extend from a single base portion (720, 722). In other versions, inactive arms (792) on one side of marker element (712) may be longer relative to inactive arms (792) on another side of marker element (712). In such versions, the length of inactive arms (792) may be varied such that inactive arms (792) may together form an interlocking relationship.

As noted above, active arms (742) may move between a pre-deployment configuration and a post-deployment configuration. Meanwhile, inactive arms (792) may remain generally stationary during the transition of active arms (742) from the pre-deployment configuration to the posit deployment configuration. FIGS. 6 and 7 show active arms (742) in the post-deployment state. In this state, each active arm (742) curves outwardly from a longitudinal axis defined by marker element (712). In other words, active arms (742) may be splayed outwardly relative to each other. Also in this state, inactive arms (792) remain in a generally straight configuration, extending along the longitudinal axis defined by marker element (712). In some versions, the outward extension, curvature, and/or splaying of active arms (742) may approximately double the diameter of marker (700) relative to the diameter when in the pre-deployment configuration. In other versions, this outward extension, curvature, and/or splaying of active arms (742) may approximately triple the diameter of marker (700) relative to the diameter when in the pre-deployment configuration.

As best seen in FIGS. 6 and 7, the particular outward curvature of each active arm (742) may be non-linear with the curvature having a relatively low slope initially, followed by a relatively high slope before reversing to a relatively low slope, followed by a relatively high slope, and finally a relatively low slope. In other words, the curvature of each active arm (742) may be approximately parabolic or bow-shaped. As can be seen, such a shape of each active arm (742) is configured with an inflection point at approximately the center of marker element (712). In some versions, the particular curvature used may be varied among active arms (742), with one or more active arms (542) having an irregular curvature, lager curvature, and/or etc., and one or more other active arms (742) having a relatively continuous curvature similar to the one shown in FIG. 6.

As described above, arms (742, 792) of the present version are integral with base portion (720). Marker element (712) is thus a single material. The particular material used in the present version is a shape-memory alloy. As will be described in greater detail below, the shape-memory characteristic of the material used in marker element (712) may be used to permit transitioning of active arms (742) from the pre-deployment configuration to the post-deployment configuration using patient heat from tissue surrounding the biopsy site to initiate the transition.

It should be understood that a variety of suitable shape-memory alloys may be used for marker element (712). In addition, the constituents of any one shape-memory alloy may be varied to produce desired properties (e.g., transformation temperature). One suitable shape-memory alloy may include Nitinol (nickel-titanium). Any suitable grade of Nitinol may be used. By way of example only, one suitable grade of Nitinol may include Nitinol S (ASTM 2063). Alternatively, other shape-memory alloys may include copper-based alloys, gold-cadmium, silver-cadmium, and/or nickel-aluminum.

Returning to FIG. 6, the entire outer surface of marker element (712) may include a surface treatment (ST). Surface treatment (ST) is generally configured to enhance the echogenicity of marker element (712). In the present version, surface treatment (ST) includes sandblasting. However, it should be understood that in other versions, various alternative surface treatments (ST) may be used. For instance, in some versions, surface treatment (ST) may include an echogenic coating having a plurality of microspheres and a polymer binder. Such a coating may be in addition to, or in lieu of, sandblasting. In addition, or in the alternative, other versions may include a roughened surface by various processing mechanisms such as peening, griding, knurling, and/or etc. Of course, various alternative configurations of surface treatment (ST) may be used as will be apparent to those of ordinary skill in the art in view of the teachings herein.

Figure 8B:
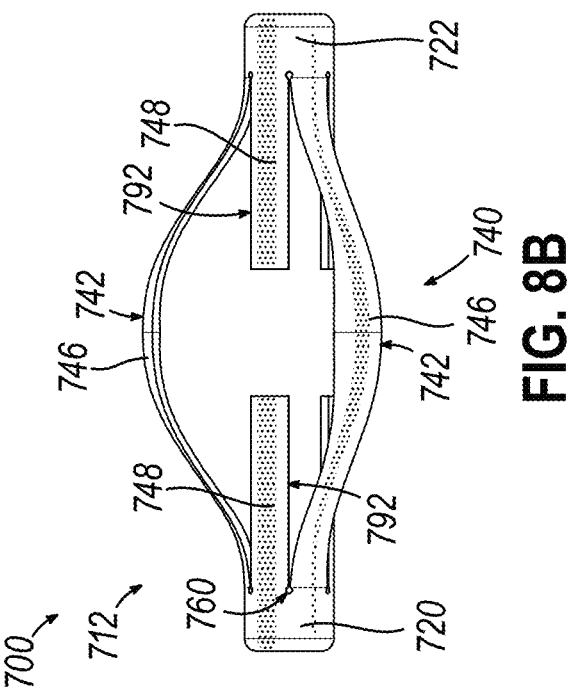
FIG. 8B depicts another side elevational view of the marker of FIG. 6, the marker being in a post-deployment configuration.
Figure 8A:
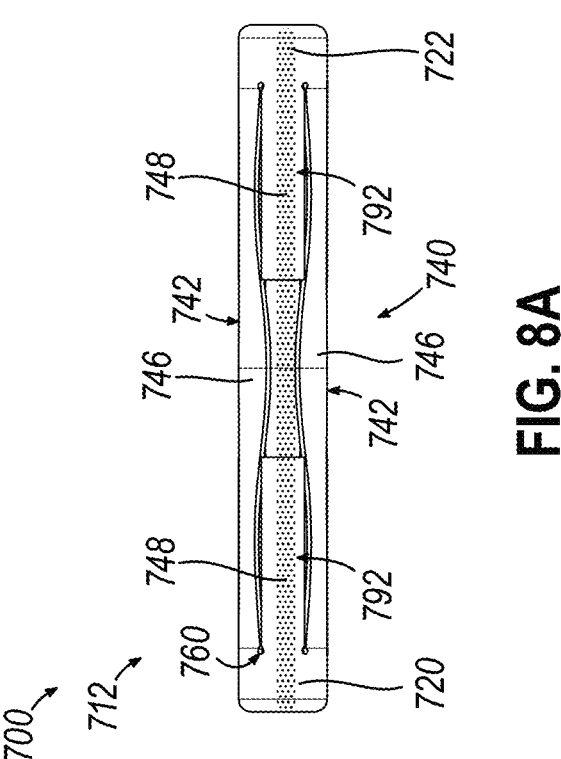
FIG. 8A depicts a side elevational view of the marker of FIG. 6, the marker being in a pre-deployment configuration.
Figure 9:
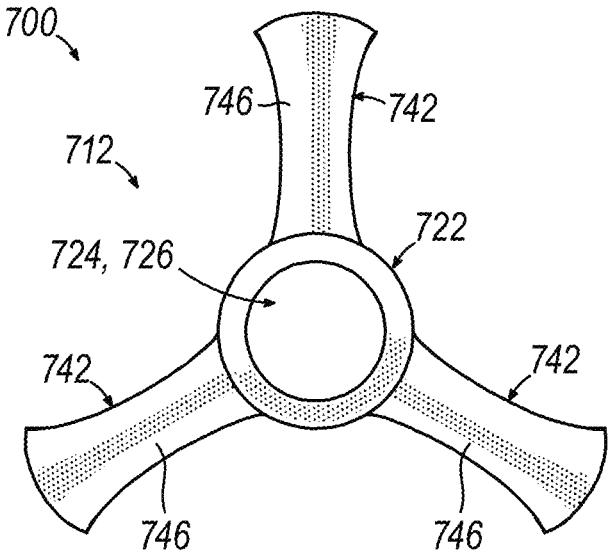
FIG. 9 depicts a front elevational view of the marker of FIG. 6, the marker being in the post-deployment configuration of FIG. 8B.

FIGS. 8A through 9 show aspects of a use of marker element (712) for marking tissue. As can be seen in FIG. 8A, marker element (712) may initially begin with active arms (742) in the pre-deployment configuration. In the pre-deployment configuration, active arms (742) may be compressed inwardly towards the longitudinal axis defined by marker element (712) so that each active arm (742) abuts each adjacent inactive arm (792). When active arms (742) are compressed as shown, arms (742, 792) together form a generally hollow cylindrical shape corresponding to the shape of base portions (720, 722). Thus, marker element (712) may define a generally cylindrical shape when active arms (742) are in the pre-deployment configuration. In some versions, the length of marker element (712) may also increase when in the pre-deployment configuration due to the compression of active arms (742) inwardly into the straight shape shown in FIG. 8A.

In some versions, the post-deployment configuration described above may correspond to a "natural," "original,"

"shape set," or "undeformed" shape. In other words, the post-deployment configuration may be the natural or as-manufactured shape of active arms (742) imparted into the shape-memory alloy. Active arms (742) may then be compressed into the pre-deployment shape shown in FIG. 8A subsequently during manufacturing to prepare marker element (712) for use in deployment at a biopsy site.

Regardless of how the transformation of active arms (742) to the pre-deployment configuration is performed, marker element (712) may be introduced into a patient at a biopsy site while in the pre-deployment configuration. In some uses, introduction of marker element (712) may be performed via marker delivery device (150) described in greater detail below. The pre-deployment configuration may be desirable for introduction at the biopsy site because the compact and uniform shape may promote use with instruments similar to marker delivery device (150) described below. The compact and uniform shape may also promote movement of marker element (712) through tissue for placement at the biopsy site.

Once marker element (712) is positioned as desired, marker element (712) may absorb heat from the tissue adjacent to the biopsy site and increase in temperature. The temperature of marker element (712) may increase until reaching a transformation temperature of the shape-memory alloy of marker element (712). Once the transformation temperature is reached, the alloy may return to its natural, original, or undeformed shape. In the present version, this shape corresponds to the post-deployment configuration of active arms (742). Thus, heat from the patient may initiate a transition of active arms (742) from the pre-deployment configuration to the post-deployment configuration.

As best seen in FIGS. 8B and 9, the transition to the post-deployment configuration includes active arms (742) moving outwardly away from the longitudinal axis defined by marker element (712). In other words, active arms (742) may spread or splay outwardly relative to each other. At the same time, the overall length of marker element (712) may decrease proportionally to the outward expansion of active arms (742). During this transition, active arms (742) may engage the tissue surrounding the biopsy site to anchor marker element (712) in the tissue, thereby holding marker element (712) in position at the biopsy site.

Throughout the transition of active arms (742) from the pre-deployment configuration to the post-deployment configuration, inactive arms (792) remain generally stationary. In particular, as best seen in FIGS. 8A and 8B, inactive arms (792) generally remain in a straight configuration throughout the transition of active arms (742) from the pre-deployment configuration to the post-deployment configuration. In this straight configuration of inactive arms (792), inactive arms (792) remain in a position extending along a longitudinal axis defined by marker element (712). In some versions, the configuration of inactive arms (792) in the straight and static configuration shown may be desirable to promote anchoring of marker (700). For instance, inactive arms (792) may provide an irregular interior profile of marker element (712), which may be used to facilitate growth of tissue among inactive arms (792).

Figure 10:
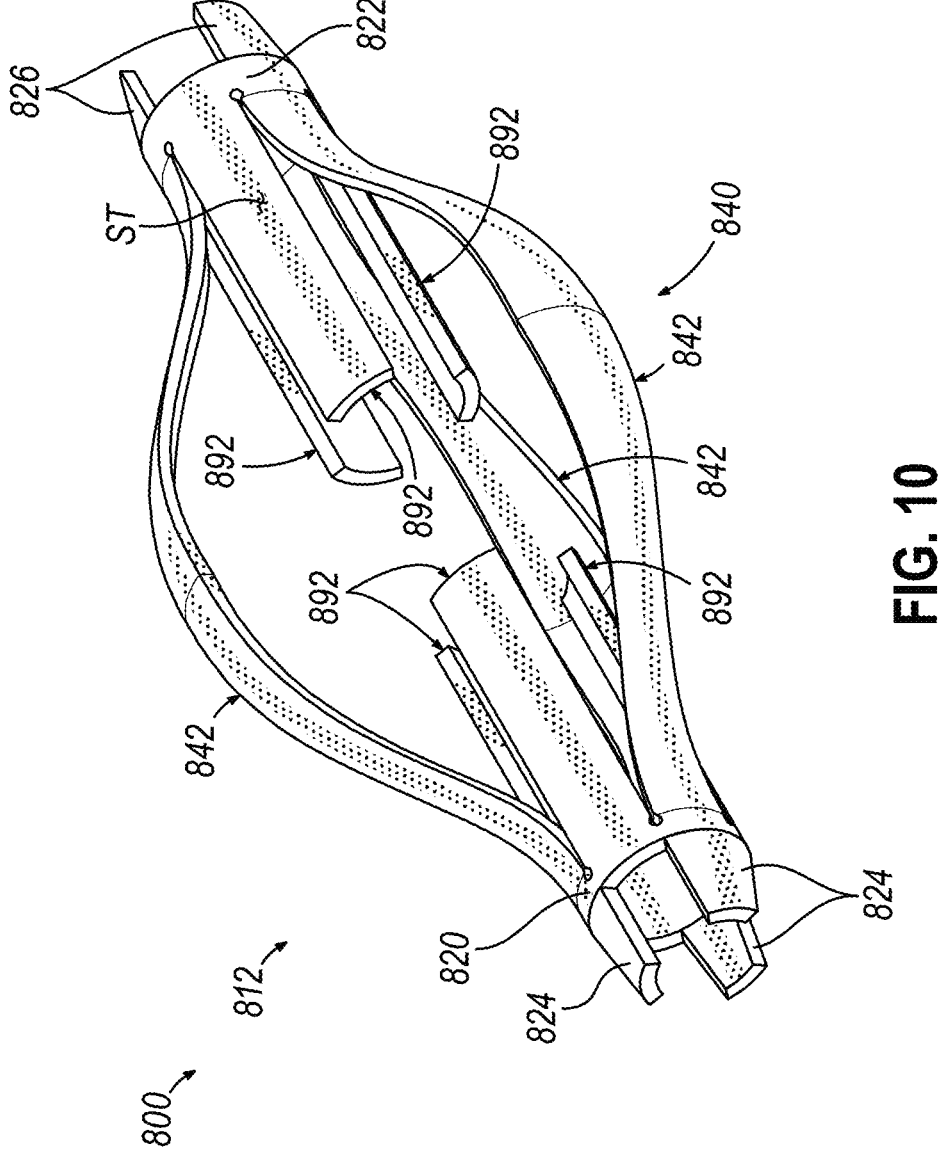
FIG. 10 depicts a perspective view of still another example of a biopsy site marker.

FIG. 10 shows another version of a biopsy site marker (800) that is substantially similar to marker (700) described above. For instance, like marker (700) described above, marker (800) of the present version includes a marker element (812) that may be used as a "bare" marker or in connection with structures similar to carrier (120) described below. As with marker element (712) described above, marker element (812) of the present version includes a distal base portion (820), a proximal base portion (822), and an anchor portion (840) extending between distal base portion (820) and proximal base portion (822) along a longitudinal axis defined by marker element (812).

Like with anchor portion (740) described above, anchor portion (840) of the present version includes a set of active arms (842) and a set of inactive arms (892) extending inwardly from each base portion (820, 822). Except as otherwise described below, arms (842, 892) are configured and function as similarly described above with respect to arms (742, 792). For instance, as with arms (742, 792) described above, arms (842, 892) of the present version may be configured such that active arms (842) may transition from a pre-deployment configuration to a post-deployment configuration, while inactive arms (792) remain in a generally stationary or static configuration.

Unlike base portions (720, 722) described above, base portions (820, 822) of the present version each include one or more static anchors (824, 826). Specifically, distal base portion (820) includes a plurality of distal static anchors (824, 826) extending outwardly from an outer side of distal base portion (820). Similarly, proximal base portion (822) includes a plurality of proximal static anchors (826) extending outwardly from an outer side of proximal base portion (822). Static anchors (824, 826) are positioned in a generally circular pattern around the cylindrical shape of each corresponding base portion (820, 822).

Each static anchor (824, 826) defines a shape generally corresponding to the shape of a small section each corresponding base portion (820, 822). In other words, each static anchor (824, 826) defines a curvature corresponding to the curvature of each corresponding base portion (820, 822). Additionally, each static anchor (824, 826) defines a taper, with the width of each static anchor (824, 826) decreasing as each static anchor (824, 826) extends from each corresponding base portion (820, 822). The extension of each static anchor (824, 826) is at a slight angle relative to the longitudinal axis of marker element (812), such that each static anchor (824, 826) is angled slightly inwardly towards the center of marker element (812).

The particular shape and configuration of static anchors (824, 826) is generally configured to provide additional anchoring of marker element (812) within tissue. For instance, static anchors (824, 826) may provide a generally irregular shape that may catch or grab adjacent tissue, thereby holding marker element (812) in position. In addition, or in the alternative, the irregular shape of static anchors (824, 826) may facilitate anchoring using the growth of tissue between each static anchor (824, 826) and into marker element (812).

II. EXEMPLARY USE OF MARKER

Figures 11A, 11B, 11C:
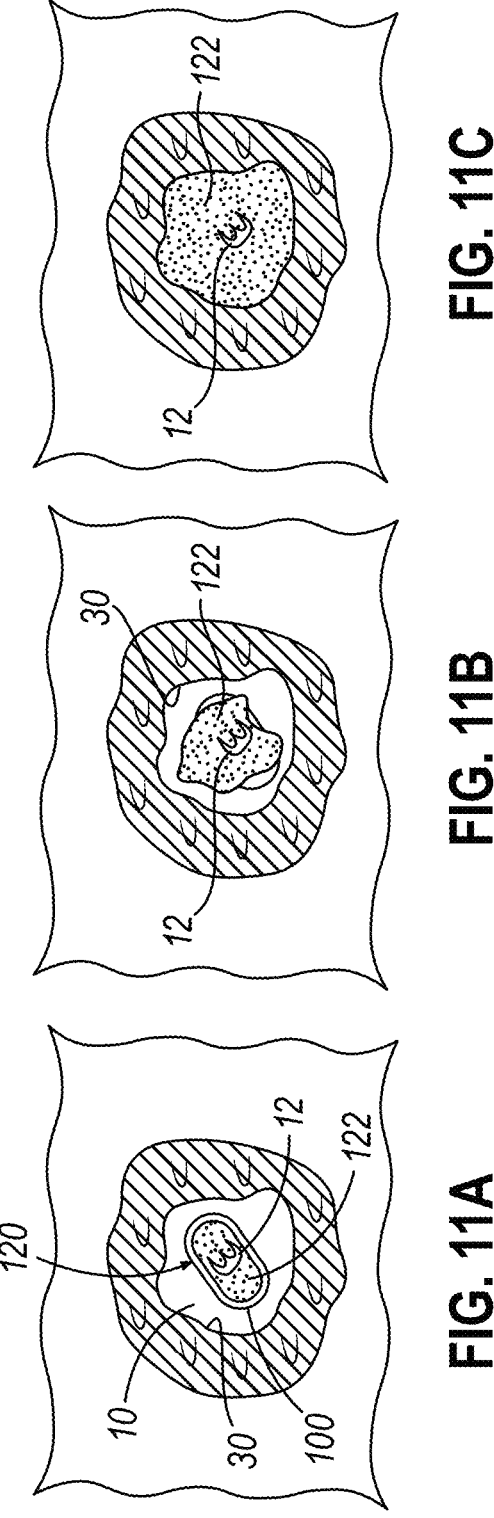
FIGS. 11A, 11B, and 11C show exemplary aspects of placement of still another biopsy site marker, in accordance with aspects of the present disclosure.

Aspects presented herein relate to devices and procedures for using a marker for percutaneously marking a biopsy cavity (10) having surrounding tissue (30), as shown in FIGS. 11A-11C. For instance, as seen in FIG. 11A, a marker (100) may be initially placed in the biopsy cavity (10) to facilitate relocation of the biopsy site. Although use described herein is in the context of marker (100), it should be understood that in some uses markers (500, 600, 700, 800) described above may be used in lieu of, or in addition to, marker (100). Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some versions, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present version, marker material (122) comprises a hydrogel that is initially in a dehydrated state. Although a hydrogel is used in the present version, it should be understood that in other versions marker material (122) may comprise other known bioab- sorbable materials. As noted above, in some versions, carrier (120) may also be used with alternative marker elements such as marker elements (512, 612, 712, 812).

In the present version, marker (100) further includes a marker element (12) that is generally not bioabsorbable (e.g., permanent or semi-permanent). Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other versions, marker (100) may be formed without a marker element (12). In still other versions, marker (100) may be formed with only marker element (12) such that carrier (120) is omitted and marker element (12) is in a "bare" form. In other words, in some versions marker (100) is formed of only marker element (12) as a bare clip or other structure and carrier (120) may be omitted entirely. As noted above, in some versions, marker element (12) may be readily replaced with any one or more of marker elements (512, 612, 712, 812) described above.

Marker material (122) is generally expandable once dis- posed within a patient at a biopsy site. As shown in FIGS. 11B and 11C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the original condition.

Markers (100, 500, 600, 700, 800) may be inserted into the body either surgically via an opening in the body cavity (30), or through a minimally invasive procedure using such devices as a catheter, introducer or similar type insertion device. Markers (100, 500, 600, 700, 800) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via markers (100, 500, 600, 700, 800).

Marker (100) of the present version is large enough to be readily visible to a clinician under x-ray or ultrasonic viewing, for example; yet small enough to be able to be percutaneously deployed into the biopsy cavity and to not cause any difficulties with the patient. Although various aspects of marker (100) are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

III. EXEMPLARY MARKER DELIVERY DEVICE

Figure 12:
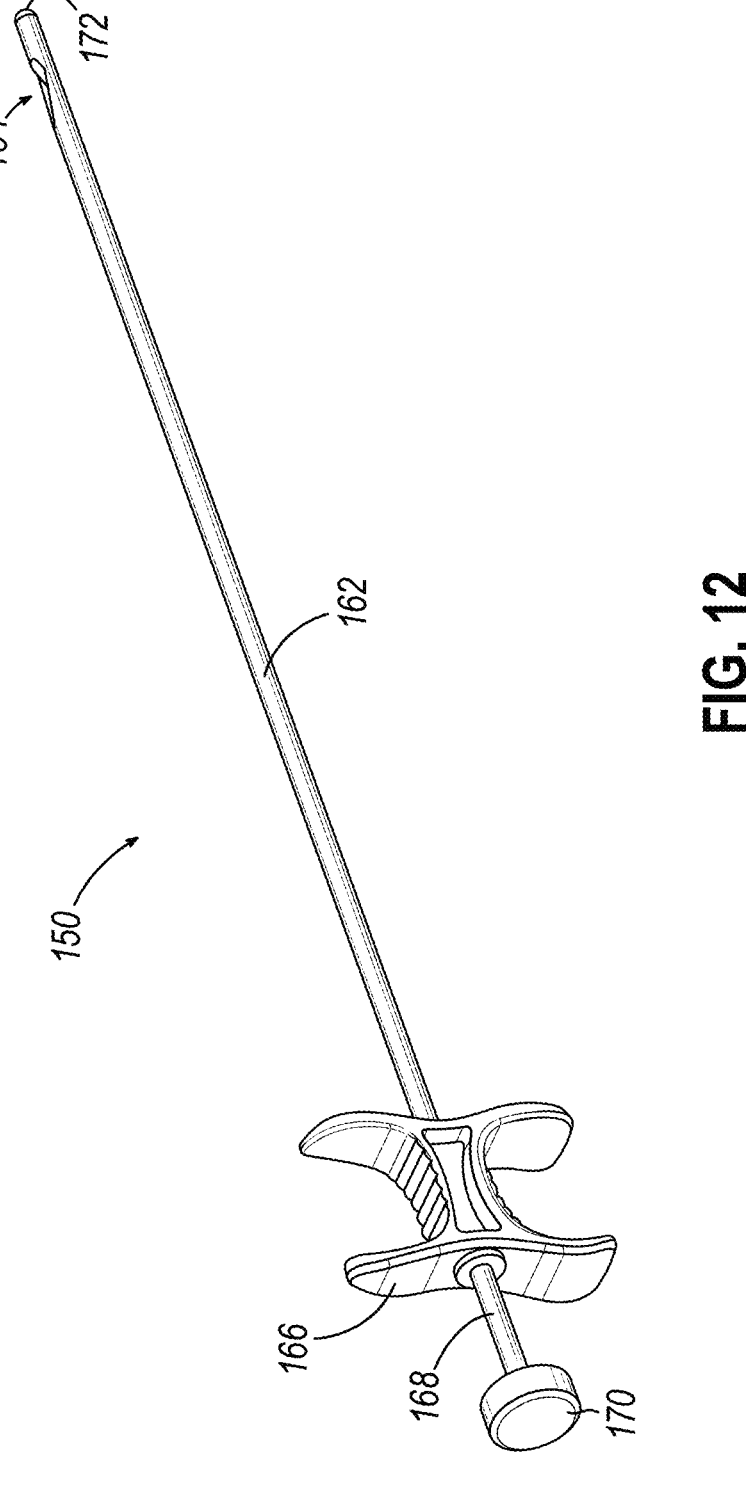
FIG. 12 depicts a perspective view of an example of a marker delivery device.

In some versions, it may be desirable to deploy any one or more of markers (100, 500, 600, 700, 800) described above within the body cavity (30) using certain marker delivery devices. For instance, FIGS. 12 and 13 show an exemplary marker delivery device (150) which includes an elongate outer cannula (162) having a marker exit, such as side opening (164) formed adjacent to, but spaced proxi- mally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 13). Rod (168) may have sufficient rigidity in compression to push a marker from an internal lumen (165) of cannula (162) out through opening (164), yet relatively flexible in bending. A plunger (170) is coupled at the proximal end of rod (168) for forcing rod (168) distally in cannula (162) to deploy a marker out of cannula (162).

A user may grasp grip (166) with two fingers, and may push on plunger (170) using the thumb on the same hand, so that marker delivery device (150) is operated by a user's single hand. A spring (not shown) or other feature may be provided about rod (168) to bias rod (168) proximally relative to grip (166) and cannula (162).

Figure 13:
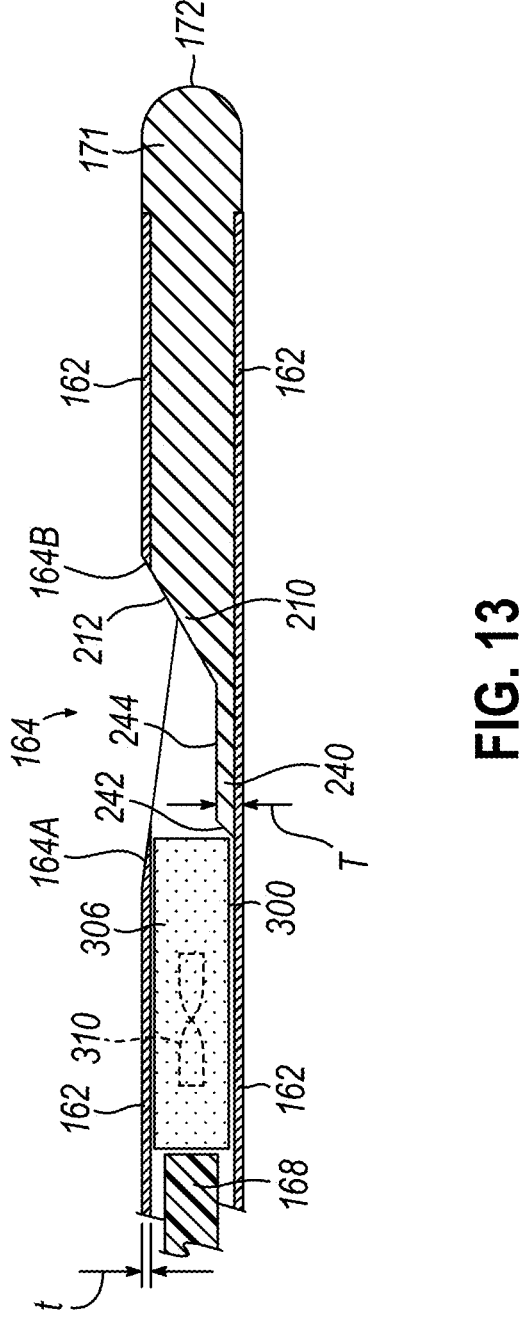
FIG. 13 depicts a side cross-sectional view of the marker delivery device of FIG. 12.

FIG. 13 shows a cross-sectional view of a distal portion of the marker delivery device (150). As can be seen, a biopsy site marker (300) similar to markers (100, 500, 600, 700, 800) described above is disposed within internal lumen (165) of cannula (162). Although marker delivery device (150) is shown and described herein as being used in connection with marker (300), it should be understood that in other uses, marker delivery device (150) may be readily used with any one or more of markers (100, 500, 600, 700, 800) in addition to, or in lieu of, marker (300). In the present version, marker (300) comprise a biodegradable or other- wise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin-walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX, and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 13.

In the present version, distal tip (172) extends from the distal end of cannula (162) and is rounded as shown in FIG. 13. Referring to FIG. 13, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 13, element (240) helps to stiffen cannula (162) in the region where wall of cannula (162) is cut to form opening (164). As shown in FIG. 13, marker engaging element (240) extends from the proximal most portion of ramp surface (212), and does not extend proximally of side opening (164), though in other embodiments, a portion of element (240) may extend proximally of opening (164).

As shown in FIG. 13, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 13) of about 45 degrees, while ramp surface (212) forms an included angle with the longitudinal axis of about 30 degrees. Of course, any number of other suitable angles may be used.

As shown in FIG. 13, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 14:
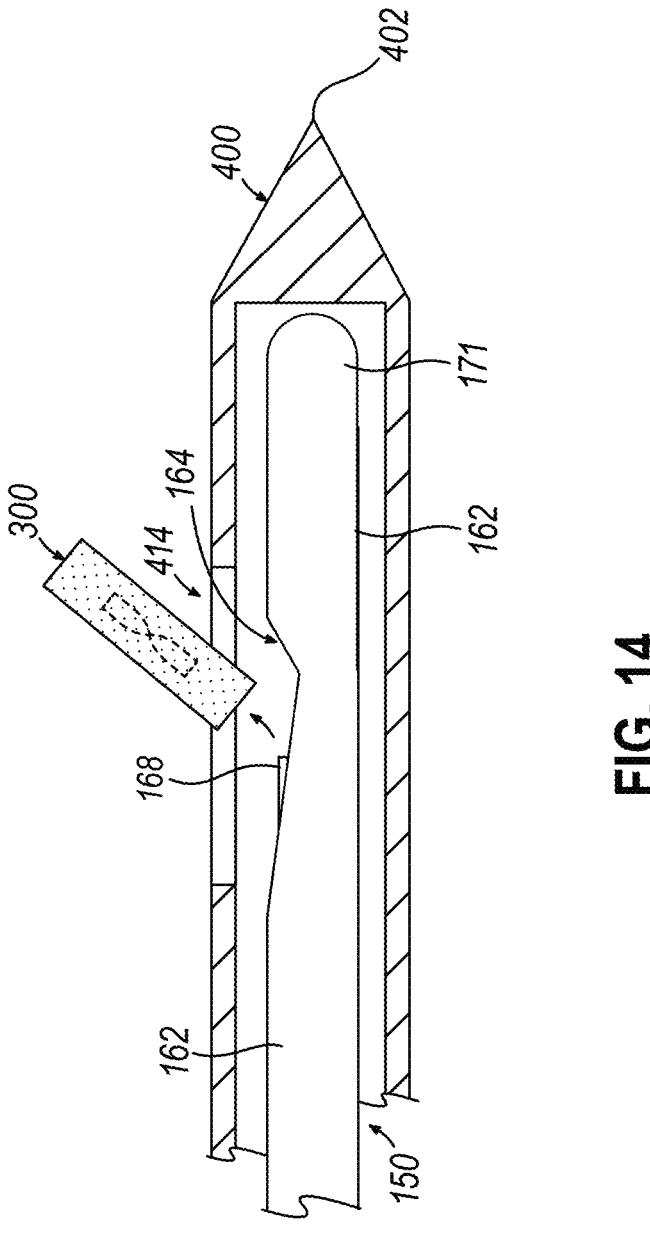
FIG. 14 depicts a cross-sectional view of still another marker being deployed from the distal portion of the marker delivery device of FIG. 11A and through a lateral aperture in a biopsy needle to mark a biopsy site.

Referring to FIG. 14, marker delivery device (150) is used to deploy a marker (300) (or alternatively markers (100, 500, 600, 700, 800)) to mark a biopsy location within a patient. In FIG. 14, a cannular biopsy needle (400) is shown having a closed distal end with piercing tip (402) and a lateral tissue receiving aperture (414). Marker delivery device (150) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 14 shows the distal end of marker delivery device (150) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (150) is inserted into a proximal opening in needle (400). In FIG. 14, needle (400) and marker delivery device (150) are positioned such that opening (164) of cannula (162) and lateral aperture (414) of needle (400) are substantially aligned axially and circumferentially. Then, with marker delivery device (150) and needle (400) so positioned at the biopsy site, push rod (168) is advanced to deploy marker (300) up ramp surface (212), through opening (164), and then through lateral aperture (414), into the biopsy cavity.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy site marker, comprising: a marker element, the marker element including a base portion and an anchor portion, the anchor portion extending from the base portion, the anchor portion including a plurality of arms, one or more arms of the plurality of arms being configured to be responsive to heat to transition from a pre-deployment configuration to a post-deployment configuration, each transitioned arm of the plurality of arms extending outwardly from a longitudinal axis defined by the marker element when in the post-deployment configuration.

Example 2

The marker of Example 1, each arm of the plurality of arms being configured to abut one or more adjacent arms when in the pre-deployment configuration.

Example 3

The marker of Examples 1 or 2, each arm of the plurality of arms being arranged in a circular pattern relative to the base portion.

Example 4

The marker of any one or more of Examples 1 through 3, each arm having a curved inner surface and a curved outer surface, the curved inner surface and the curved outer surface of each arm of the plurality of arms being configured to form a hollow cylindrical shape when the plurality of arms are in the pre-deployment configuration.

Example 5

The marker of any one or more of Examples 1 through 4, the base portion including a first base portion and a second base portion, one or more arms of the plurality of arms extending from the first base portion to the second base portion.

Example 6

The marker of any one or more of Examples 1 through 5, each transitioned arm of the plurality of arms defining a curved exponential or parabolic shaped profile when in the post-deployment configuration.

Example 7

The marker of any one or more of Examples 1 through 6, the marker element being configured to slidably engage a cannula when each transitioned arm of the plurality of arms are in the pre-deployment configuration.

Example 8

The marker of any one or more of Examples 1 through 7, the plurality of arms including three or more arms.

Example 9

The marker of any one or more of Examples 1 through 8, the marker element defining a plurality of relief openings, each relief opening being disposed between an arm of the plurality of arms, each relief opening being configured to permit movement of each arm relative to the base portion.

Example 10

The marker of any one or more of Examples 1 through 9, the plurality of arms including a plurality of active arms and a plurality of inactive arms, the plurality of active arms being configured to transition from the pre-deployment configuration to the post-deployment configuration while the plurality of inactive arms remain substantially stationary.

Example 11

The marker of any one or more of Examples 1 through 10, each arm of the plurality of arms being integral with the base portion.

Example 12

The marker of any one or more of Examples 1 through 11, the base portion having a hollow interior and an open end, the open end of the base portion being configured to promote tissue in-growth.

Example 13

The marker of any one or more of Examples 1 through 12, the marker element including a surface treatment to one or more exterior surfaces of the marker element, the surface treatment being configured to increase echogenicity of the marker element.

Example 14

The marker of Example 13, the surface treatment including a sand blasted surface.

Example 15

The marker of any one or more of Examples 1 through 14, the marker element being configured as a bare marker element.

Example 16

A biopsy site marker, the biopsy site marker comprising: a base portion; and an anchor portion extending from at least one side of the base portion, the anchor portion including a plurality of engagement arms, each engagement arm having a shape set position and a compressed position, each engagement arm being splayed from each other engagement arm when in the shape set position, each engagement arm being configured to return to the shape set position from the compressed position when the anchor portion is exposed to a predetermined temperature.

Example 17

The biopsy site marker of Example 16, the base portion including a distal base portion and a proximal base portion, each engagement arm of the plurality of engagement arms extending from the distal base portion to the proximal base portion.

Example 18

The biopsy site marker of Example 16, one or more engagement arms of the plurality of engagement arms extending from a proximal and distal side of the base portion, the base portion being centered between at least two engagement arms of the plurality of engagement arms.

Example 19

The biopsy site marker of any one or more of Examples 16 through 18, the anchor portion defining a first diameter when each engagement arm is in the compressed position, the anchor portion defining a second diameter when each engagement arm is in the shape set position, the second diameter being at least double the first diameter.

Example 20

The biopsy site marker of any one or more of Examples 16 through 18, the anchor portion defining a first diameter when each engagement arm is in the compressed position, the anchor portion defining a second diameter when each engagement arm is in the shape set position, the second diameter being at least triple the first diameter.

Example 21

The biopsy site marker of any one or more of Examples 16 through 20, further comprising a plurality of static arms, each static arm of the plurality of static arms being configured to remain in a static position relative to the engagement arms.

Example 22

The biopsy site marker of Example 21, each static arm of the plurality of static arms extending along a longitudinal axis defined by the biopsy site marker.

Example 23

The biopsy site marker of Examples 21 or 22, each static arm of the plurality of static arms defining a length shorter than a length defined by each engagement arm of the plurality of engagement arms.

Example 24

The biopsy site marker of Examples 21 or 22, each static arm of the plurality of static arms defining a length longer than a length defined by each engagement arm of the plurality of engagement arms.

Example 25

A biopsy site marker, comprising: a marker element, the marker element defining a hollow cylindrical shape extending from a proximal end to a distal end, the marker element further defining a plurality slots extending longitudinally relative to a longitudinal axis of the marker element to define a plurality of active arms and a plurality of passive arms, each active arm of the plurality of active arms being configured to move outwardly from the longitudinal axis defined by the marker element in response to heat at a biopsy site.

Example 26

The biopsy site marker of Example 25, the plurality of slots extending inwardly towards a base portion disposed between at least two active arms and at least two passive arms.

Example 27

The biopsy site marker of Example 25, the plurality of slots extending inwardly from a distal base portion to a proximal base portion to define each active arm such that each active arm extends from the distal base portion to the proximal base portion.

Example 28

The biopsy site marker of Example 27, the distal base portion and the proximal base portion each including a plurality of static anchors, the static anchors extending outwardly from the distal base portion and the proximal base portion, respectively.

Example 29

The biopsy site marker of any one or more of Examples 25 through 28, the plurality of slots terminating in a relief opening, the relief opening being sized to permit movement of the active arms relative to a portion of the marker element.

Example 30

The biopsy site marker of any one or more of Examples 25 through 29, the marker element including a single material, the single material being Nitinol.

Example 31

A biopsy marking system, the system comprising: a biopsy site marker of any one or more of Examples 1 through 30; a marker delivery device, the marker delivery device including an introducer cannula, a grip, and a push rod, the introducer cannula being configured to receive the marker, the push rod being configured to move relative to the grip to eject the marker from a marker exit defined by the introducer cannula.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy site marker, comprising:
a marker element, the marker element including a base portion and an anchor portion,
the anchor portion extending from the base portion, the anchor portion including a plurality of arms,
the plurality of arms including a plurality of active arms and a plurality of inactive arms, the plurality active of arms being configured to be responsive to heat to transition from a pre-deployment configuration to a post-deployment configuration,
each active arm of the plurality of active arms extending outwardly from a longitudinal axis defined by the marker element when in the post-deployment configuration, each active arm of the plurality of active arms being aligned with the longitudinal axis when in the pre-deployment configuration,
the plurality of active arms being configured to transition from the pre-deployment configuration to the post-deployment configuration while the plurality of inactive arms remain in a stationary configuration with each inactive arm being aligned with the longitudinal axis,
each arm of the plurality of arms having a curved inner surface and a curved outer surface, the curved inner surface and the curved outer surface of each arm of the plurality of arms being configured to form a hollow cylindrical shape when the plurality of arms are in the pre-deployment configuration.

2. The marker of claim 1, each arm of the plurality of arms being configured to abut one or more adjacent arms when in the pre-deployment configuration.

3. The marker of claim 1, each arm of the plurality of arms being arranged in a circular pattern relative to the base portion.

4. The marker of claim 1, the base portion including a first base portion and a second base portion, one or more arms of the plurality of arms extending from the first base portion to the second base portion.

5. The marker of claim 1, each transitioned arm of the plurality of arms defining a curved exponential or parabolic shaped profile when in the post-deployment configuration.

6. The marker of claim 1, the marker element being configured to slidably engage a cannula when each transitioned arm of the plurality of arms are in the pre-deployment configuration.

7. The marker of claim 1, the plurality of arms including three or more arms.

8. The marker of claim 1, the marker element defining a plurality of relief openings, each relief opening being disposed between a pair of arms of the plurality of arms, each relief opening being configured to permit movement of each arm relative to the base portion.

9. The marker of claim 1, each arm of the plurality of arms being integral with the base portion.

10. The marker of claim 1, the base portion having a hollow interior and an open end, the open end of the base portion being configured to promote tissue in-growth.

11. The marker of claim 1, the marker element including a surface treatment to one or more exterior surfaces of the marker element, the surface treatment being configured to increase echogenicity of the marker element.

12. The marker of claim 11, the surface treatment including a sand blasted surface.

13. The marker of claim 1, the marker element being configured as a bare marker element.

14. A biopsy site marker, the biopsy site marker comprising:
a base portion; and
an anchor portion extending from at least one side of the base portion, the anchor portion including a plurality of engagement arms and a plurality of static arms,
each engagement arm having a shape set position and a compressed position, each engagement arm being splayed from each other engagement arm when in the shape set position, a portion of each engagement arm being laterally offset relative to a longitudinal axis of the biopsy site marker when in the shape set position,
each engagement arm being configured to return to the shape set position from the compressed position when the anchor portion is deployed at a biopsy site,
each static arm of the plurality of static arms being configured to remain in a single static position relative to the engagement arms, each engagement arm being parallel relative to each static arm and the longitudinal axis when each engagement arm is in the compressed position,
the anchor portion including a shape memory alloy defining the plurality of engagement arms, and
each engagement arm and static arm having a curved inner surface and a curved outer surface, the curved inner surface and the curved outer surface of each engagement arm and each static arm being configured to form a hollow cylindrical shape when the engagement arms and the static arms are in the compressed position.

15. The biopsy site marker of claim 14, the base portion including a distal base portion and a proximal base portion, each engagement arm of the plurality of engagement arms extending from the distal base portion to the proximal base portion.

16. The biopsy site marker of claim 14, one or more engagement arms of the plurality of engagement arms extending from a proximal side of the base portion in one direction and a distal side of the base portion in another direction, the base portion being centered between at least two engagement arms of the plurality of engagement arms.

17. The biopsy site marker of claim 14, the anchor portion defining a first diameter when each engagement arm is in the compressed position, the anchor portion defining a second diameter when each engagement arm is in the shape set position, the second diameter being at least double the first diameter.

* * * * *